(12) United States Patent  (10) Patent No.: US 7,631,660 B2
deCler et al.  (45) Date of Patent: Dec. 15, 2009

(54) ASEPTIC COUPLING DEVICES

(75) Inventors: Charles Peter deCler, Edina, MN (US); John Russell Boehm, Eden Prairie, MN (US); Brent Paul Bushnell, Edina, MN (US)

(73) Assignee: Colder Products Company, St. Paul, MN (US)

( * ) Notice: Subject to any disclaimer, the term of this patent is extended or adjusted under 35 U.S.C. 154(b) by 116 days.

(21) Appl. No.: 11/748,819

(22) Filed: May 15, 2007

(65) Prior Publication Data

US 2008/0067807 A1 Mar. 20, 2008

Related U.S. Application Data

(60) Provisional application No. 60/747,259, filed on May 15, 2006.

(51) Int. Cl.
*F16L 29/00* (2006.01)
(52) U.S. Cl. .............................. 137/614.03; 137/614.05; 251/149.1
(58) Field of Classification Search .............................. 137/614.03–614.05; 251/149.1
See application file for complete search history.

(56) References Cited

U.S. PATENT DOCUMENTS

| | | | |
|---|---|---|---|
| 4,019,512 | A | 4/1977 | Tenczar |
| 4,022,205 | A | 5/1977 | Tenczar |
| 4,030,494 | A | 6/1977 | Tenczar |
| 4,617,012 | A | 10/1986 | Vaillancourt |
| 4,856,823 | A | 8/1989 | Heren |
| 4,982,761 | A | 1/1991 | Kreczko et al. |
| 5,029,904 | A | 7/1991 | Hunt |
| 5,393,101 | A | 2/1995 | Matkovich |
| 5,628,726 | A | 5/1997 | Cotter |
| 5,762,646 | A | 6/1998 | Cotter |
| 5,810,398 | A | 9/1998 | Matkovich |
| 5,868,433 | A | 2/1999 | Matkovich |
| 6,089,540 | A | 7/2000 | Heinrichs et al. |
| 6,161,578 | A * | 12/2000 | Braun et al. ........... 137/614.03 |
| 6,220,570 | B1 * | 4/2001 | Heinrichs et al. ........ 251/149.6 |
| 6,341,802 | B1 | 1/2002 | Matkovich |
| 6,679,529 | B2 | 1/2004 | Johnson et al. |
| 6,978,800 | B2 * | 12/2005 | deCler et al. ........... 137/614.05 |
| 7,044,161 | B2 * | 5/2006 | Tiberghien ............. 137/614.05 |

FOREIGN PATENT DOCUMENTS

DE 197 15 899 A1 10/1998

(Continued)

OTHER PUBLICATIONS

BioQuate Disposable Aseptic Connector, BioQuate Incorporated, 3 pages, http://www.bioquate.com/disposable.html (© 2003).

(Continued)

*Primary Examiner*—Kevin L Lee
(74) *Attorney, Agent, or Firm*—Merchant & Gould P.C.

(57) ABSTRACT

An aseptic coupling device includes a first state in which fluid does not flow through the aseptic coupling device. In addition, the aseptic coupling device includes a second state in which fluid does flow through the aseptic coupling device. The aseptic coupling device can be moved from first, second, and third states to control the flow of fluid through the aseptic coupling device.

11 Claims, 22 Drawing Sheets

FOREIGN PATENT DOCUMENTS

WO          WO 96/21120          7/1996

OTHER PUBLICATIONS

Applications for OEM Customers, BioQuate Incorporated, 3 pages, http://www.bioquate.com/applications.html (© 2003).

Disposable Aseptic Connector, Frequently Asked Questions, BioQuate Incorporated, 3 pages, http://www.bioquate.com/faqs.html (© 2003).

International Search Report mailed Nov. 7, 2007.

* cited by examiner

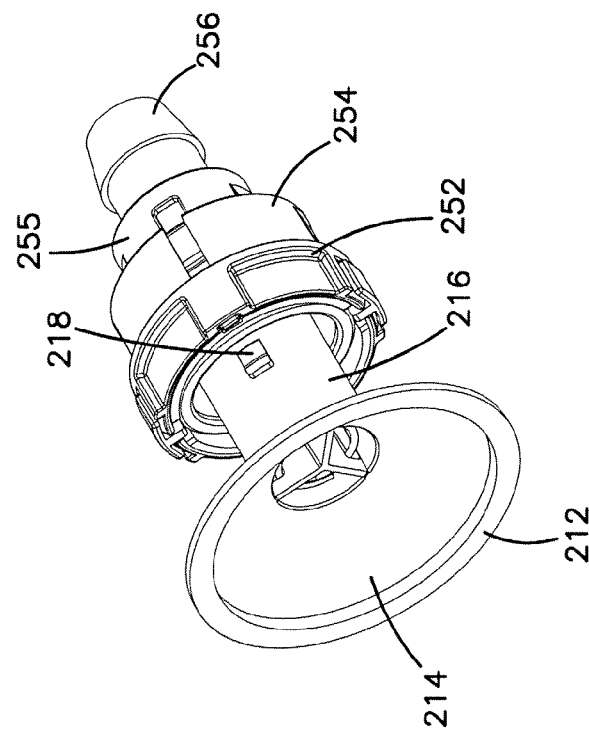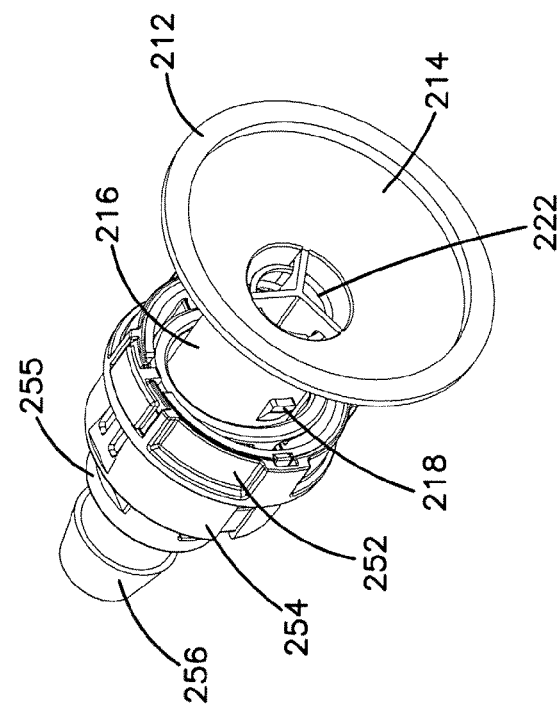

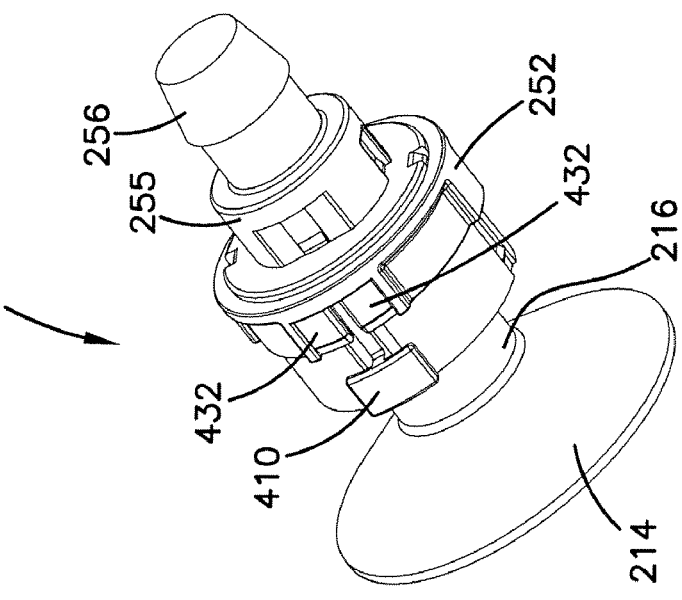
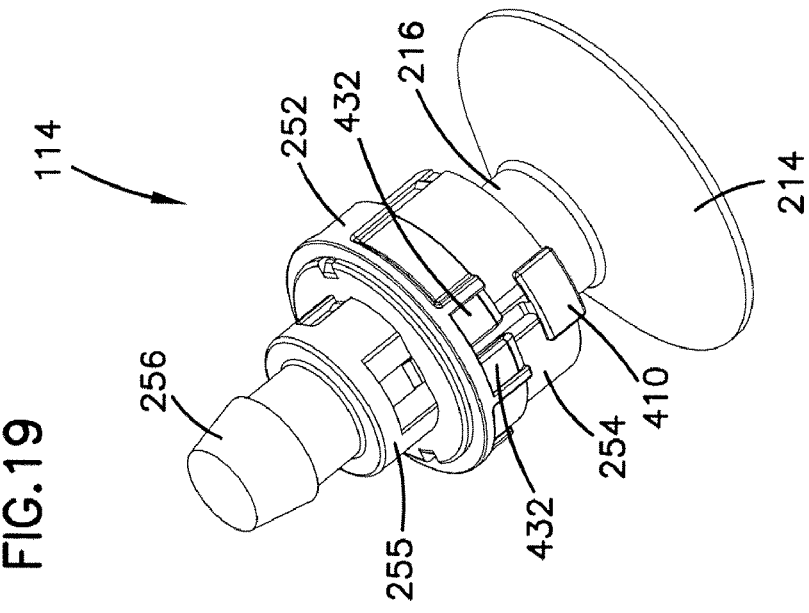

ASEPTIC COUPLING DEVICES

BACKGROUND

Aseptic coupling devices can be used to connect two or more sterilized pathways. For example, aseptic coupling devices can be used to couple a fluid pathway from a first piece of processing equipment to a fluid pathway from a second piece of processing equipment to establish a sterile pathway for fluid transfer between the first and second pieces of equipment.

Typical aseptic coupling devices require a "dry-to-dry" or "dry connection" that is created through the use of one or more pathway clamping devices placed upstream of the aseptic coupling devices so that the aseptic coupling devices are kept free of fluid while the connection between the aseptic coupling devices is made. Once the sterile connection between the aseptic coupling devices is made, the clamping devices are removed to allow fluid to flow through the aseptic coupling devices.

In typical aseptic coupling devices, a "wet connection" (i.e., in the presence of fluid) between aseptic coupling devices cannot be made. Further, once the connection between the aseptic coupling devices is made and the clamping devices are removed, there are no provisions to allow for the stopping of the flow of fluid therethrough or disconnection.

SUMMARY

The present disclosure relates to aseptic coupling devices. In example embodiments disclosed herein, an aseptic coupling device includes a first state in which fluid does not flow through the aseptic coupling device. In addition, the aseptic coupling device includes a second state in which fluid does flow through the aseptic coupling device, and a third state in which fluid does not flow through at least a portion of the aseptic coupling device. In some embodiments, the aseptic coupling device can be moved from the first, second, and third states to control the flow of fluid through the aseptic coupling device.

DESCRIPTION OF THE DRAWINGS

Reference will now be made to the accompanying drawings, which are not necessarily drawn to scale, and wherein:

FIG. 7 shows another perspective view of the aseptic coupling device of FIG. 5.

FIG. 8 shows another perspective view of the aseptic coupling device of FIG. 5.

FIG. 19 shows a perspective view of the aseptic coupling device of FIG. 12 with a collar member in a retracted position.

FIG. 20 shows another perspective view of the aseptic coupling device of FIG. 19.

DETAILED DESCRIPTION

Example embodiments will now be described more fully hereinafter with reference to the accompanying drawings. These embodiments are provided so that this disclosure will be thorough and complete. Like numbers refer to like elements throughout.

As used herein, the term "aseptic" means freedom, to a specified degree, from microorganisms. In one example embodiment, the degree of freedom from microorganisms is measured to a concentration of $1 \times 10^6$ colony forming units (CFU). As used herein, the term "sterile" is synonymous with the term "aseptic." As used herein, the term "fluid" means any substance that can be made to flow including, but is not limited to, liquids, gases, granular or powdered solids, mixtures or emulsions of two or more fluids, suspensions of solids within liquids or gases, etc.

In example embodiments, the sterility of various components can be achieved using one or more sterilization techniques, including Gamma, E-beam, ethylene oxide (EtO), and/or Autoclave technologies.

Figure 1:
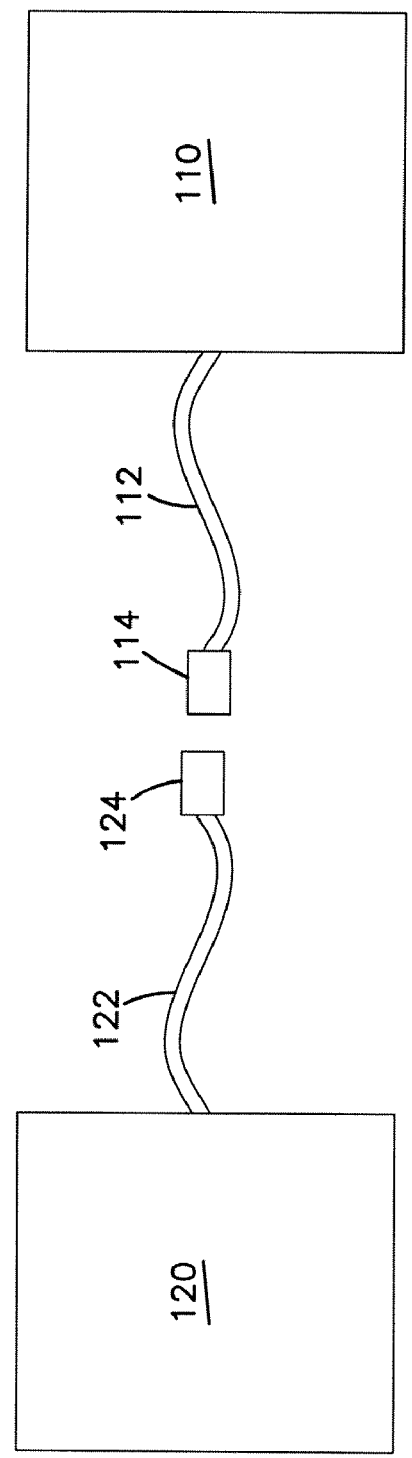
FIG. 1 shows a schematic view of an example system including first and second pieces of processing equipment and aseptic coupling devices forming a sterile connection therebetween.

Referring now to FIG. 1, an example system 100 is shown. System 100 includes a first piece of processing equipment 110 and a second piece of processing equipment 120. In example embodiments, equipment 110, 120 are bioreactors including biomaterial. In other embodiments, equipment 110, 120 can be other apparatuses that require a sterile connection therebetween such as, for example, a reactor and a media bag or other receptacle.

Equipment 110 includes a fluid pathway 112 extending therefrom that is terminated by a first aseptic coupling device 114. Likewise, equipment 120 includes a fluid pathway 122 extending therefrom that is terminated by a first aseptic coupling device 124. In example embodiments, the environment within pathways 112, 122 and aseptic coupling devices 114, 124 is sterile.

Aseptic coupling device 114 can be connected to aseptic coupling device 124. In example embodiments, aseptic coupling devices 114, 124 are genderless. In other embodiments, aseptic coupling devices 114, 124 are male and female connectors, respectively. Once aseptic coupling device 114 is connected to aseptic coupling device 124, a sterile fluid pathway is established between equipment 110 and equipment 120. Once the sterile fluid pathway is established, fluid can be transferred from equipment 110 to equipment 120, or vice versa.

Figure 2:
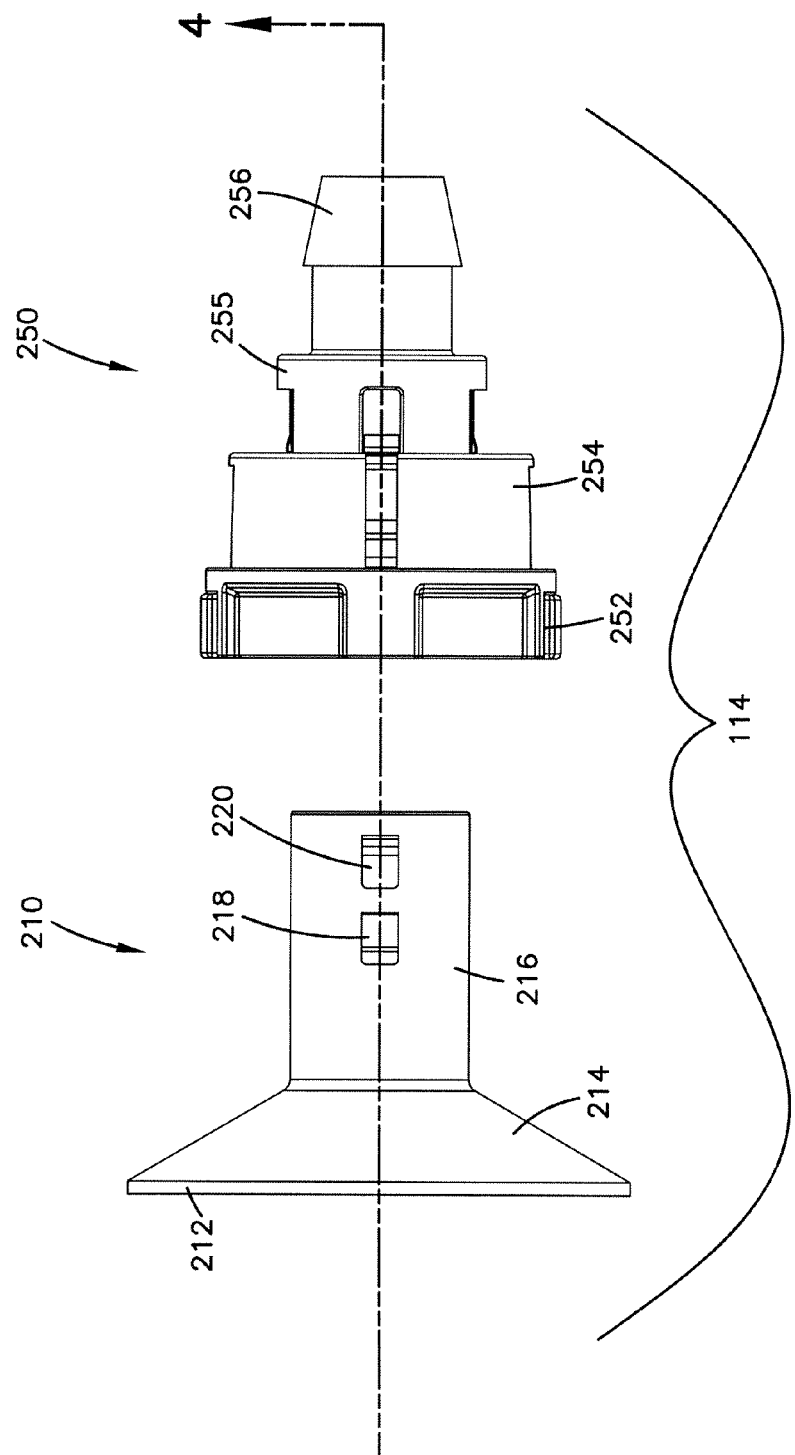
FIG. 2 shows an exploded side view of an example aseptic coupling device.
Figure 3:
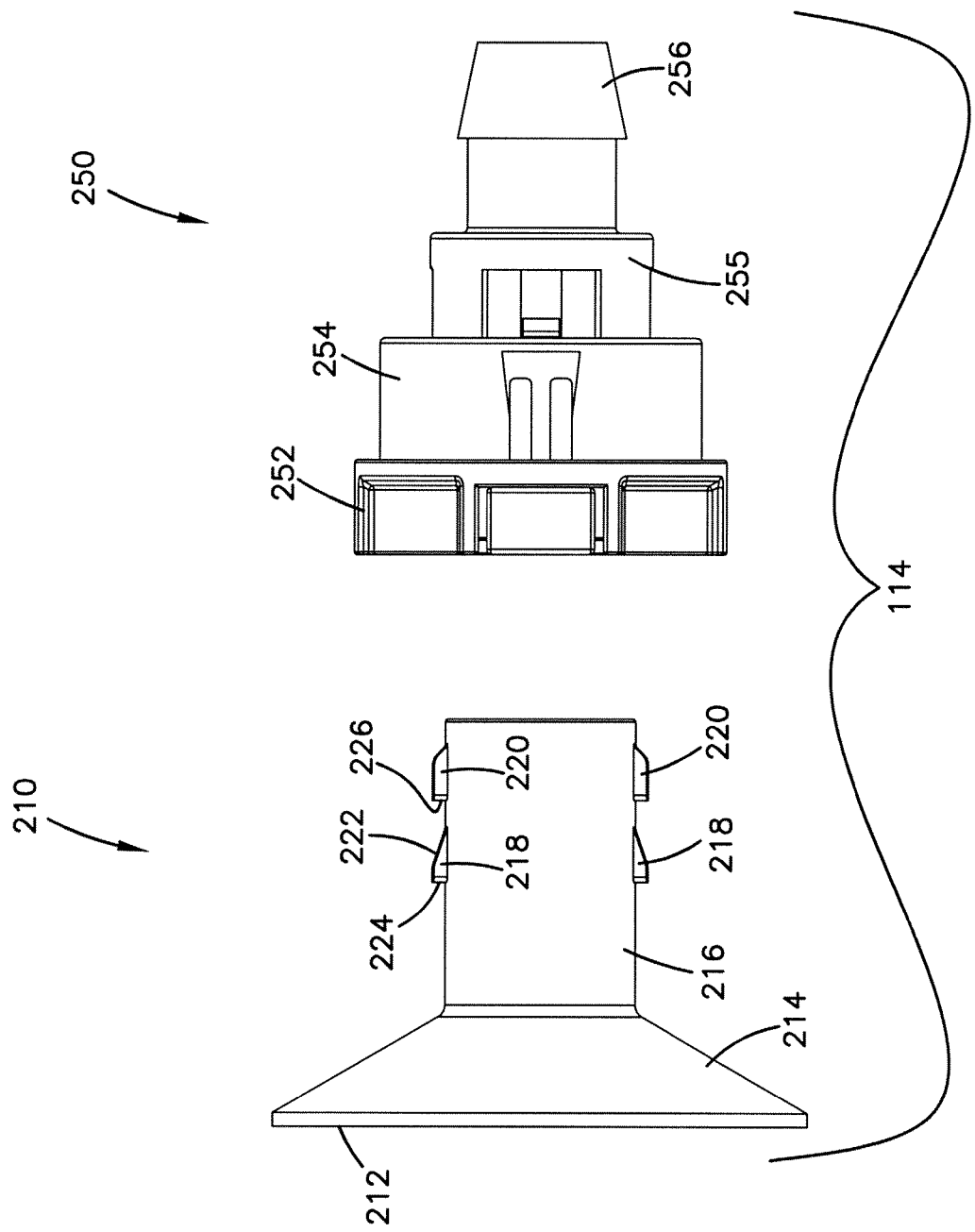
FIG. 3 shows another exploded side view of the aseptic coupling device of FIG. 2.
Figure 4:
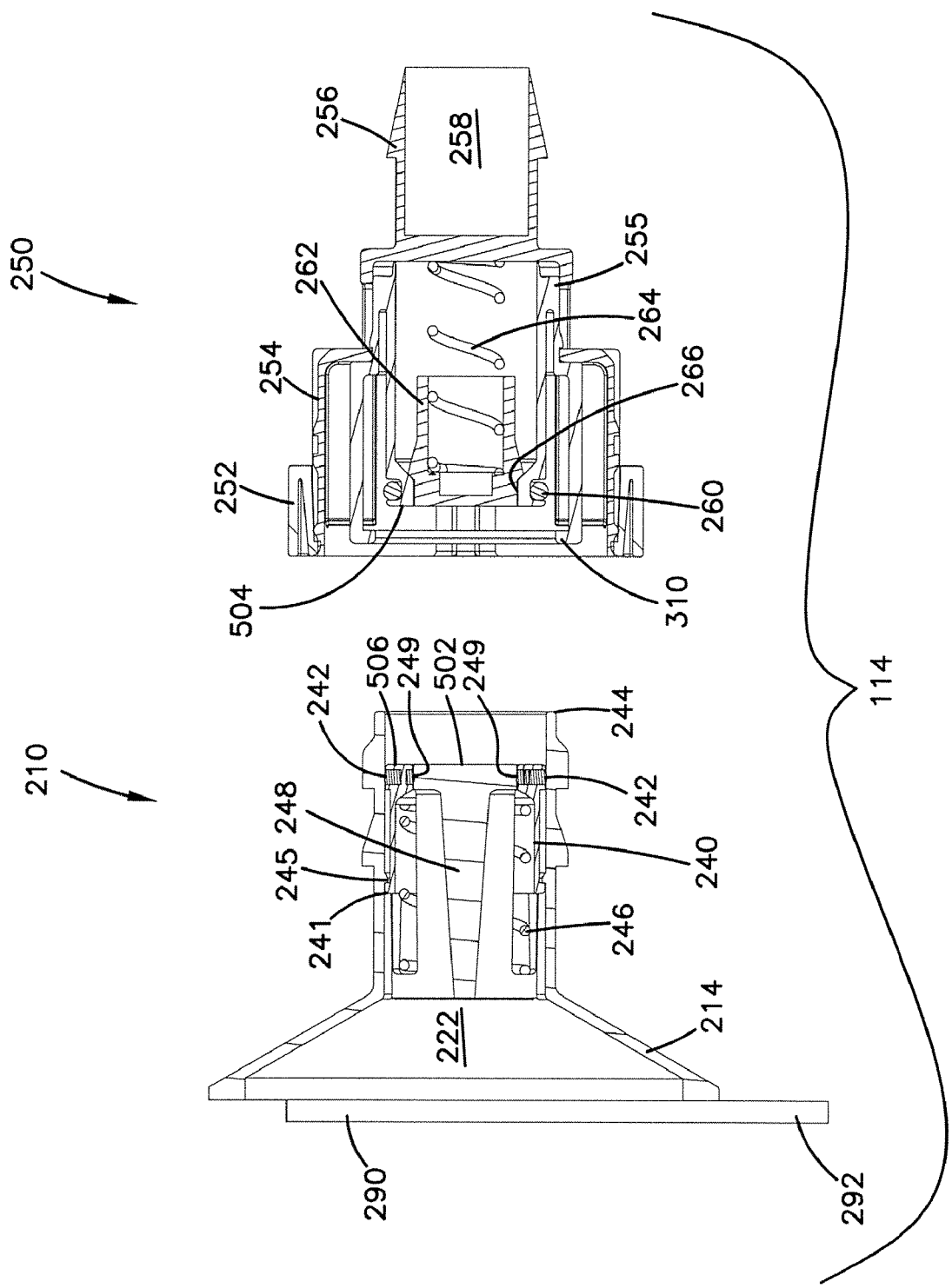
FIG. 4 shows a cross-sectional view of the aseptic coupling device of FIG. 2 along line 4-4.
Figure 6:
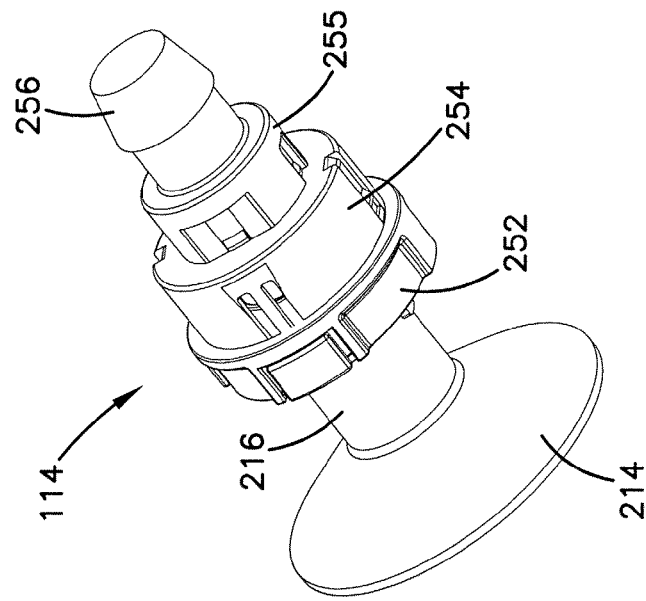
FIG. 6 shows another perspective view of the aseptic coupling device of FIG. 5.
Figure 5:
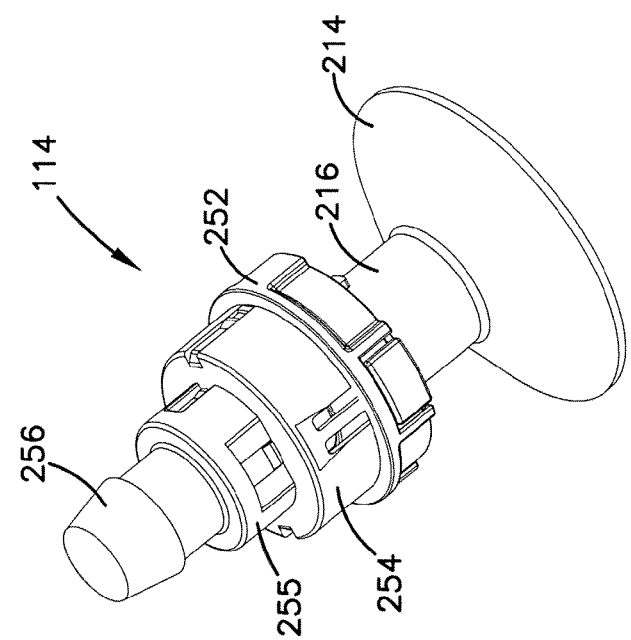
FIG. 5 shows a perspective view of the aseptic coupling device of FIG. 2 in a shipped state.
Figure 9:
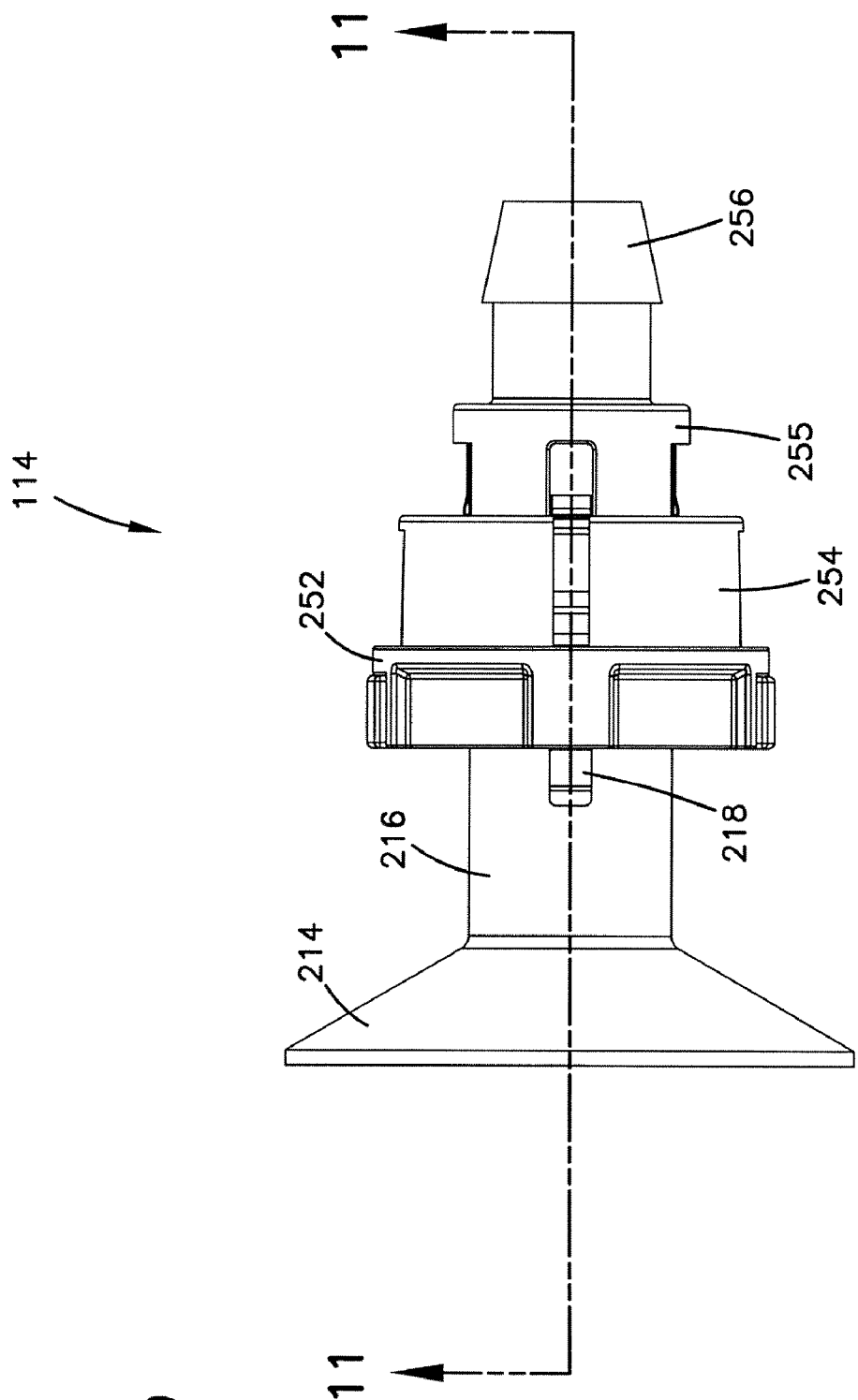
FIG. 9 shows a side view of the aseptic coupling device of FIG. 5.
Figure 10:
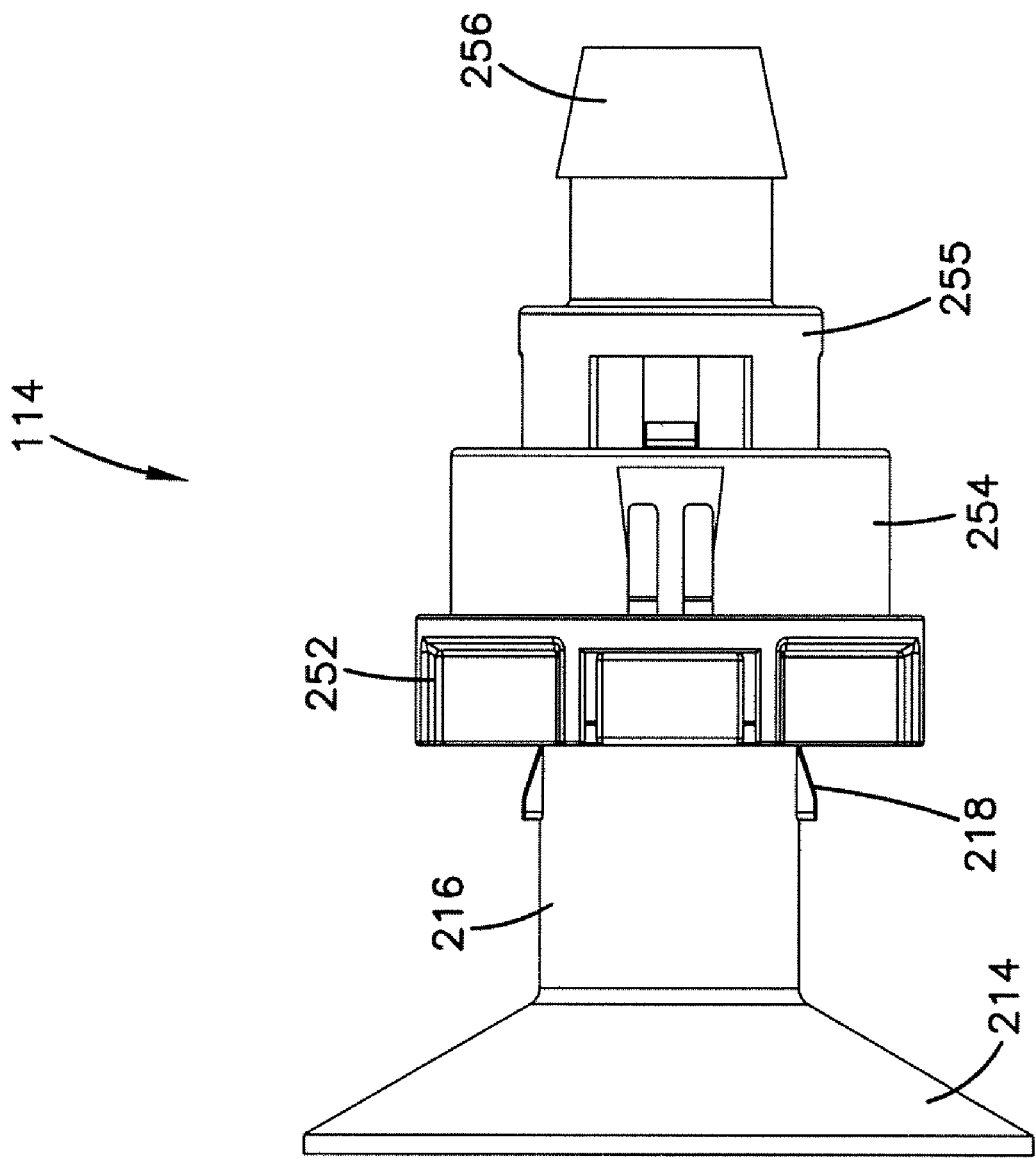
FIG. 10 shows another side view of the aseptic coupling device of FIG. 9.
Figure 11:
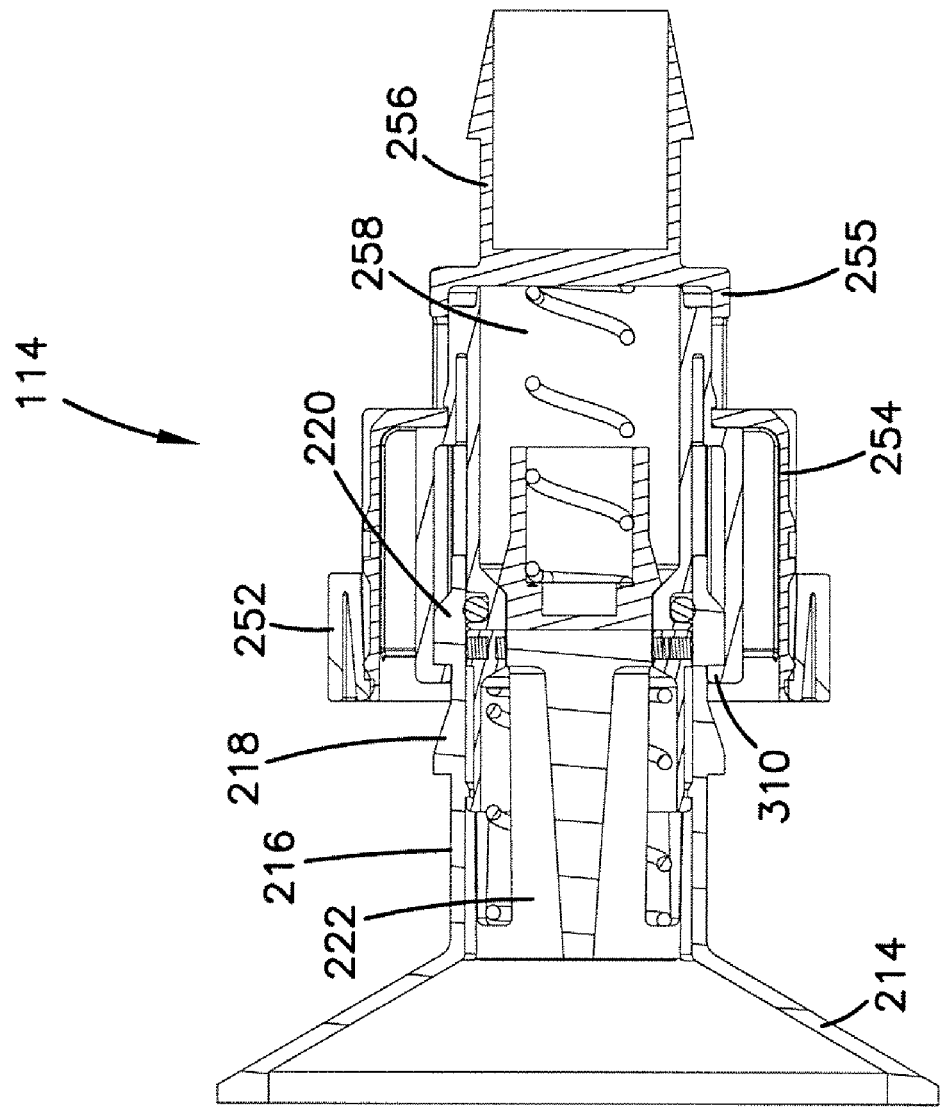
FIG. 11 shows a cross-sectional view of the aseptic coupling device of FIG. 9 along line 11-11.
Figure 13:
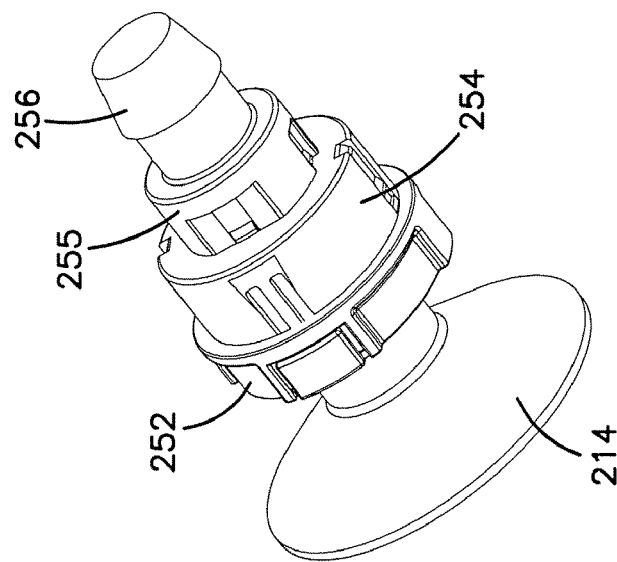
FIG. 13 shows another perspective view of the aseptic coupling device of FIG. 12.
Figure 12:
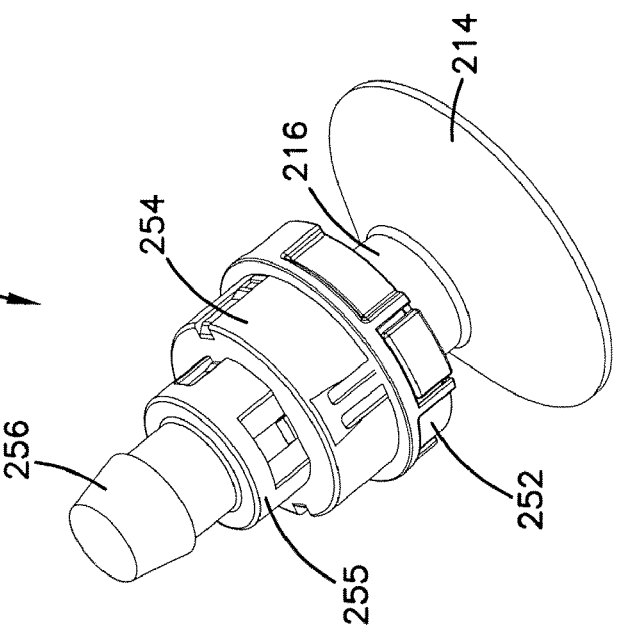
FIG. 12 shows a perspective view of the aseptic coupling device of FIG. 2 in a flow state.
Figure 15:
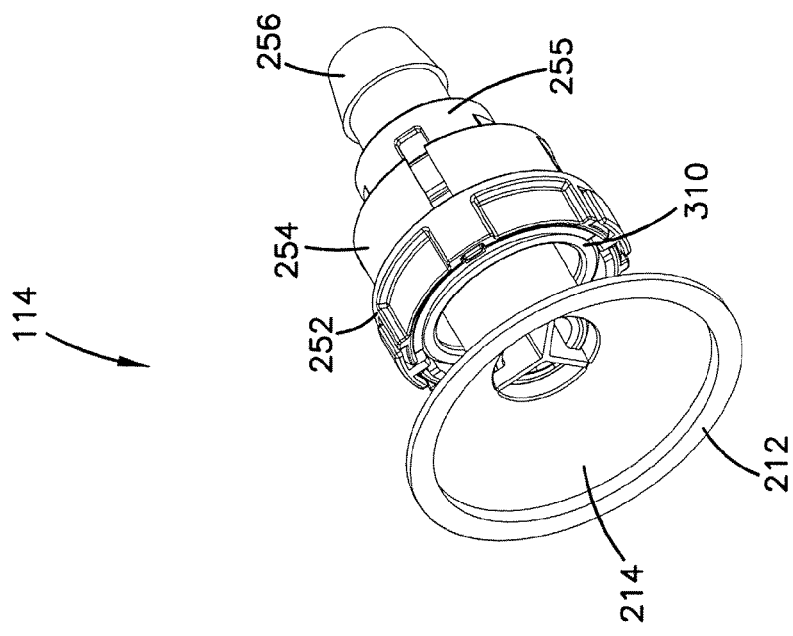
FIG. 15 shows another perspective view of the aseptic coupling device of FIG. 12.
Figure 14:
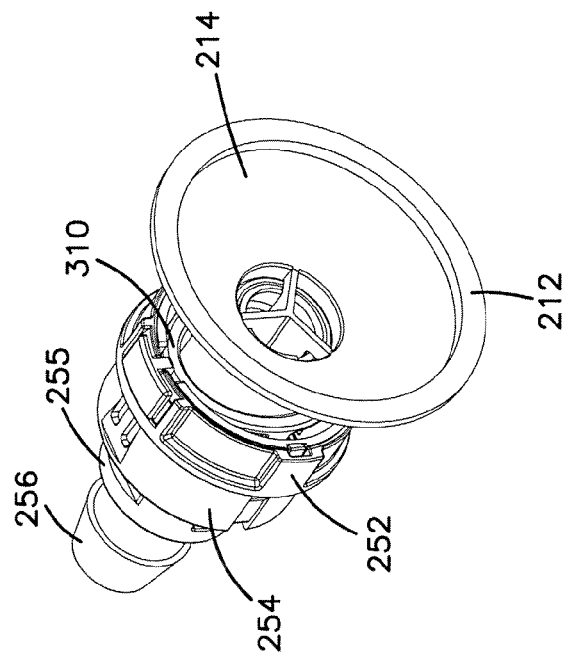
FIG. 14 shows another perspective view of the aseptic coupling device of FIG. 12.
Figure 16:
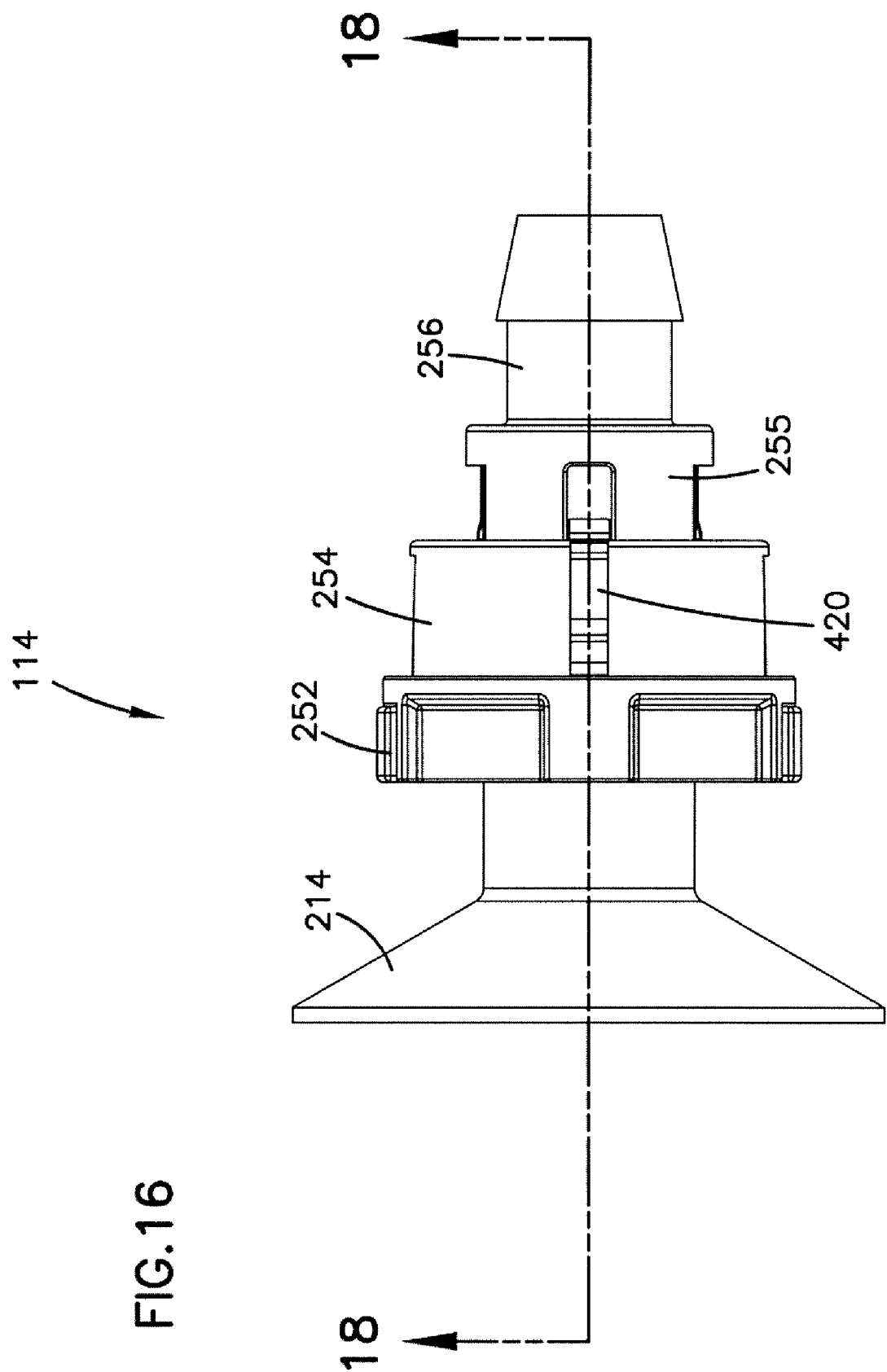
FIG. 16 shows a side view of the aseptic coupling device of FIG. 12.
Figure 17:
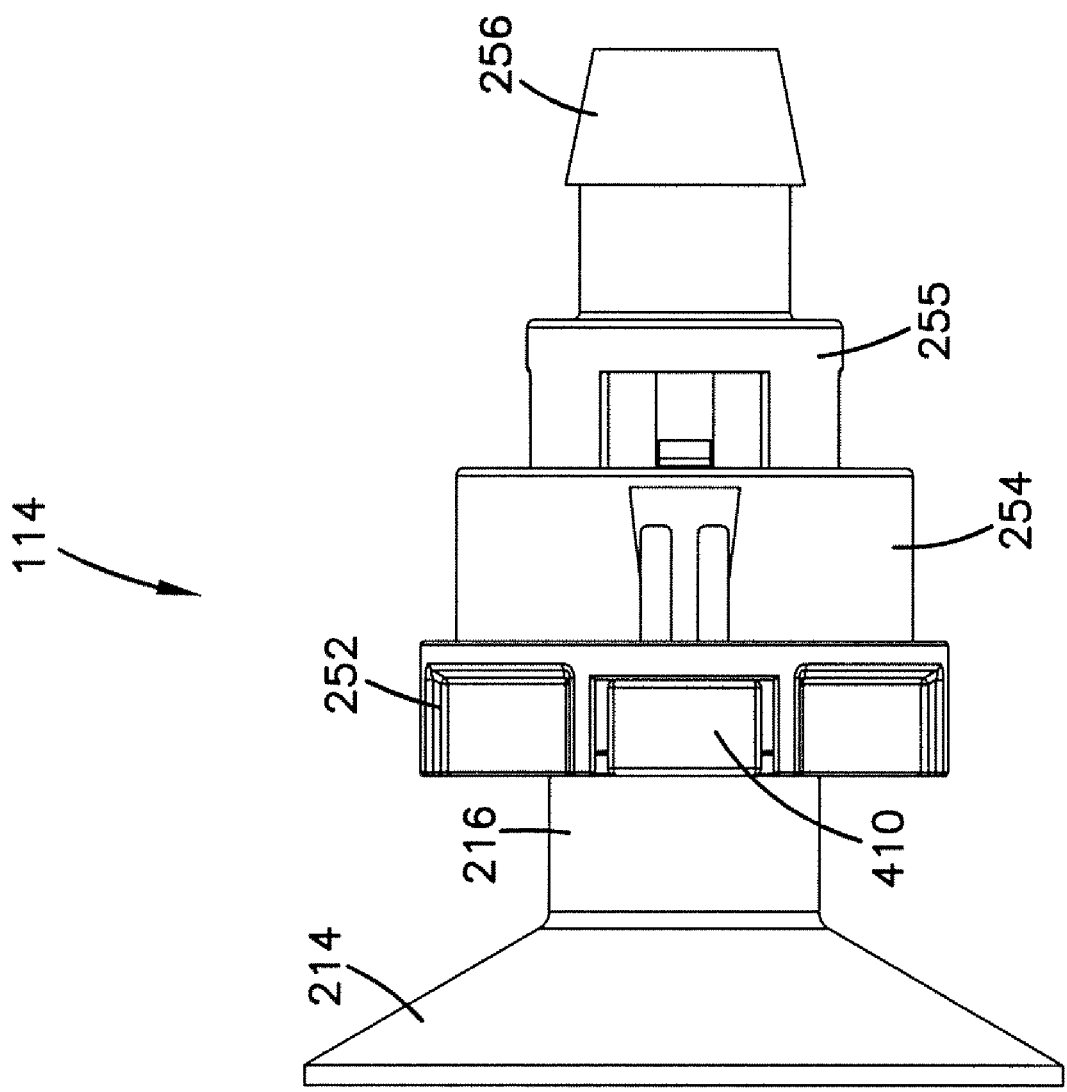
FIG. 17 shows another side view of the aseptic coupling device of FIG. 16.

Referring now to FIGS. 2-4, aseptic coupling device 114 is shown. Aseptic coupling device 114 includes a first portion 210 and a second portion 250. First portion 210 includes a front portion 214 with a face 212 configured to be connected to a mating aseptic coupling device, such as aseptic coupling device 124, as described below. First portion 210 also includes a main body 216 with barbs 218, 220 formed thereon. A fluid path 222 is formed through front portion 214 and main body 216 of first portion 210.

Positioned within main body 216 is a valve member 240 including a sealing portion 242 that seals against an interior surface 244 of main body 216. A spring 246 moves valve member 240 axially so that a barb 241 formed on valve member 240 contacts a notch 245 formed in interior surface 244 to define the closed position shown in FIG. 4. Another sealing portion 249 of valve member 240 seals against a member 248 positioned within main body 216.

Second portion 250 of aseptic coupling device 114 includes a front portion 254 and a main body 255. A collar portion 252 is positioned about front portion 254 and can be slid axially with respect to front portion 254, as described below. A barb portion 256 of second portion 250 is configured to be connected to a fluid pathway (e.g., fluid pathway 112) such as a fluid line or piece of processing equipment. A fluid path 258 is formed through front portion 254 and main body 255.

Intermediate to front portion 254 within fluid path 258 is a sealing portion 260 that is positioned to seal against internal surface 244 of main body 216 of first portion 210 when second portion 250 is connected thereto, as described below. A valve member 262 positioned with main body 255 is moved by a spring 264 into contact with seat portion 266 formed by main body 255.

Referring now to FIGS. 5-11, aseptic coupling device 114 is shown in a shipped state. In this state, first portion 210 is connected to second portion 250. Main body 216 of first portion 210 is received within front portion 254 and main body 255 of second portion 250. In this position, ends 226 (see FIG. 3) of barbs 218 formed on main body 216 of first portion 210 engage a front lip 310 formed by main body 255 of second portion 250 to connect first portion 210 to second portion 250.

In the shipped state, fluid path 222 of first portion 210 and fluid path 258 of second portion 250 are sealed by valve members 240, 262, respectively, so that fluid path 222 is not in communication with fluid path 258. Further, barb portion 256 can be connected to a fluid pathway prior to shipment and the entire assembly sterilized. In this manner, the sterility of fluid paths 222, 258 is maintained while aseptic coupling device 114 is in the shipped state.

In example embodiments, an outer wrap such as a plastic or other polymer is applied to aseptic coupling device 114 when aseptic coupling device 114 is in the shipped state. The outer wrap can be used, for example, to maintain aseptic coupling device 114 in the shipped state prior to removal of the plastic. For example, in one embodiment, shrink wrap is formed on the outer exposed surfaces of first and second portions 210, 250 of aseptic coupling device 114. The shrink wrap is removed before aseptic coupling device 114 can be moved from the shipped state to a flow state, as described below.

Aseptic coupling device 114 can be connected to a mating aseptic coupling device (e.g., aseptic coupling device 124) while in the shipped state to form a sterile connection. For example, in some embodiments, aseptic coupling device 114 includes an apparatus 290 (see FIG. 4) connected to front surface 212 that is used to create a sterile connection with a mating aseptic coupling device. Such a sterile connection is made by removing any shrink wrap and dust capping from aseptic coupling device 114 and aligning aseptic coupling device 114 with the mating aseptic coupling device. As front surface 212 of aseptic coupling device 114 contacts the front surface of the mating aseptic coupling device, an adhesive of apparatus 290 connects the coupling devices. Tabs 292 of aseptic coupling device 114 and the mating aseptic coupling device are thereby aligned. The exposed tabs 292 are pulled to cause a membrane of apparatus 290 to roll together out of aseptic coupling device 114 and the mating aseptic coupling device. The membranes can be removed complete and discarded, thereby creating the sterile connection. A sanitary clamp can be used to clamp front surfaces 212 of aseptic coupling device 114 and the mating aseptic coupling device together to maintain the connection.

In example embodiments, a Disposable Aseptic Connector manufactured by BioQuate Incorporated of Clearwater, Fla., and/or disclosed in U.S. Pat. No. 6,679,529 to Johnson et al., which is hereby incorporated by reference in its entirety, can be used as front portion 214 of first portion 210. In other embodiments, a KLEENPACK connector manufactured by Pall Corporation of East Hills, N.Y., and/or disclosed in U.S. Pat. No. 6,341,802 to Matkovich, which is hereby incorporated by reference in its entirety, can be used. In other embodiments, other aseptic connectors can be used.

Referring now to FIGS. 12-18, once aseptic coupling device 114 is mated with another aseptic coupling device, first portion 210 can be moved axially with respect to second portion to position aseptic coupling device 114 into the flow state. As aseptic coupling device 114 is moved from the shipped state to the flow state, front lip 310 of main body 255 of second portion 250 rides over a ramped portion 222 (see FIG. 3) of barbs 218 until front lip 310 slips beyond barbs 218 to engage ends 224 to lock second portion 250 to first portion 210 in the flow state.

Figure 18:
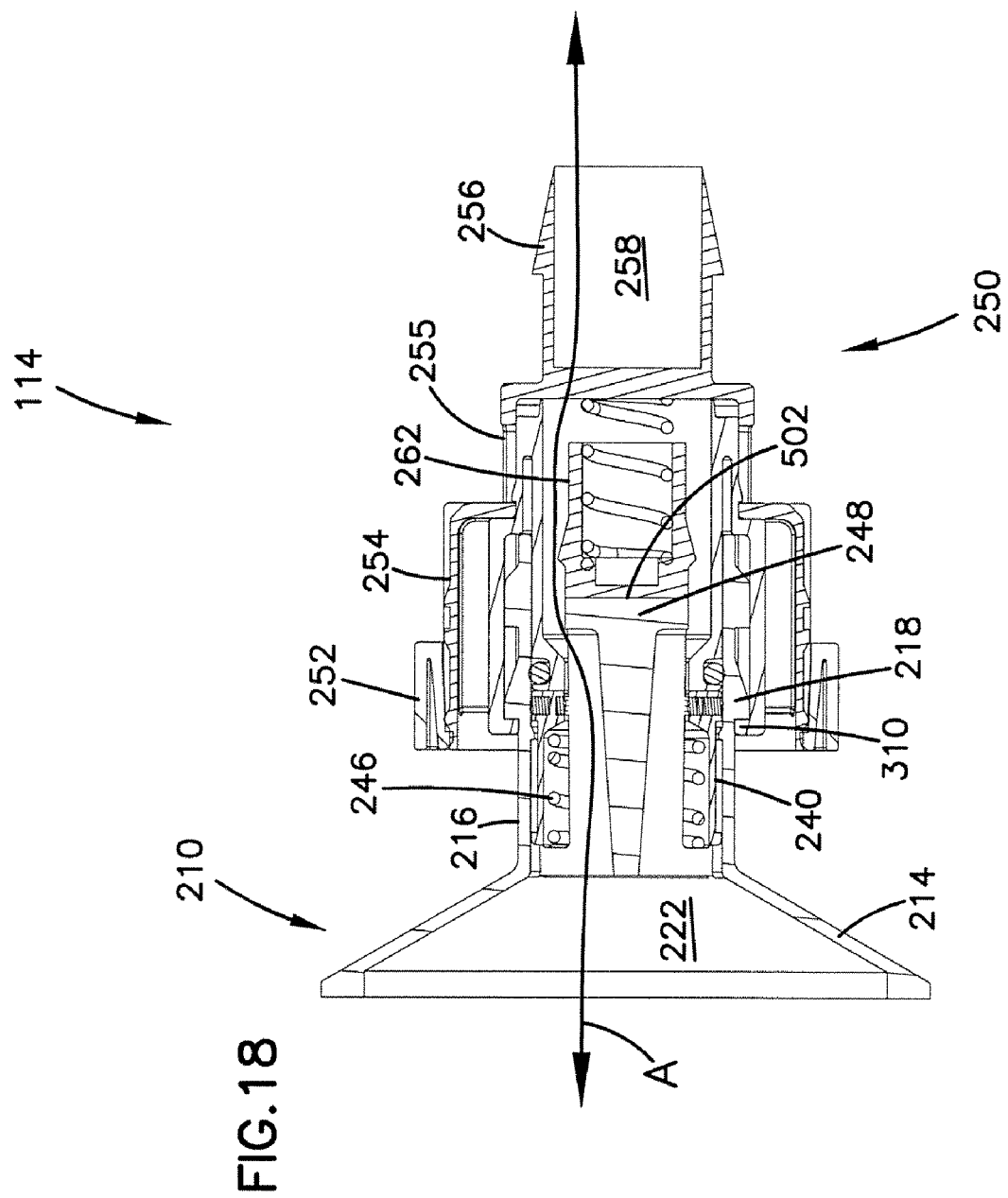
FIG. 18 shows a cross-sectional view of the aseptic coupling device of FIG. 16 along line 18-18.
Figure 22:
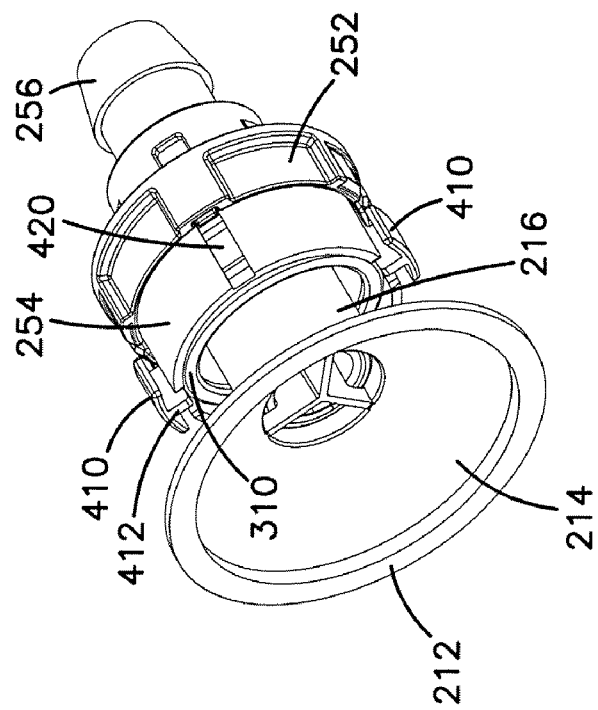
FIG. 22 shows another perspective view of the aseptic coupling device of FIG. 19.
Figure 21:
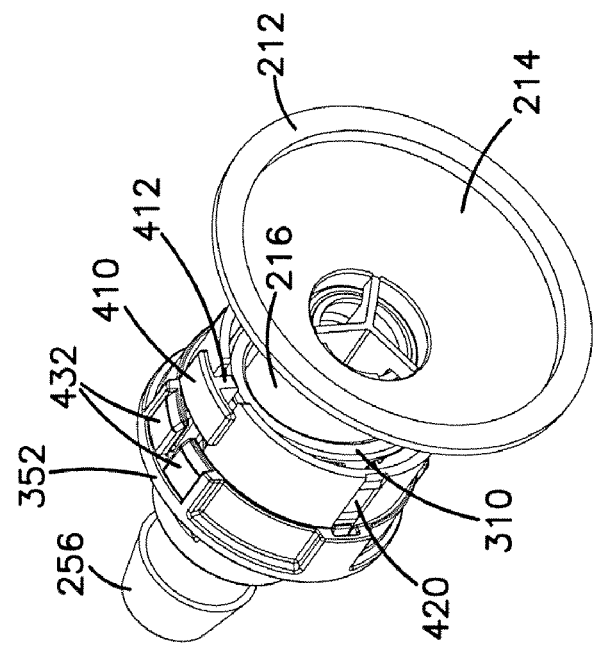
FIG. 21 shows another perspective view of the aseptic coupling device of FIG. 19.
Figure 23:
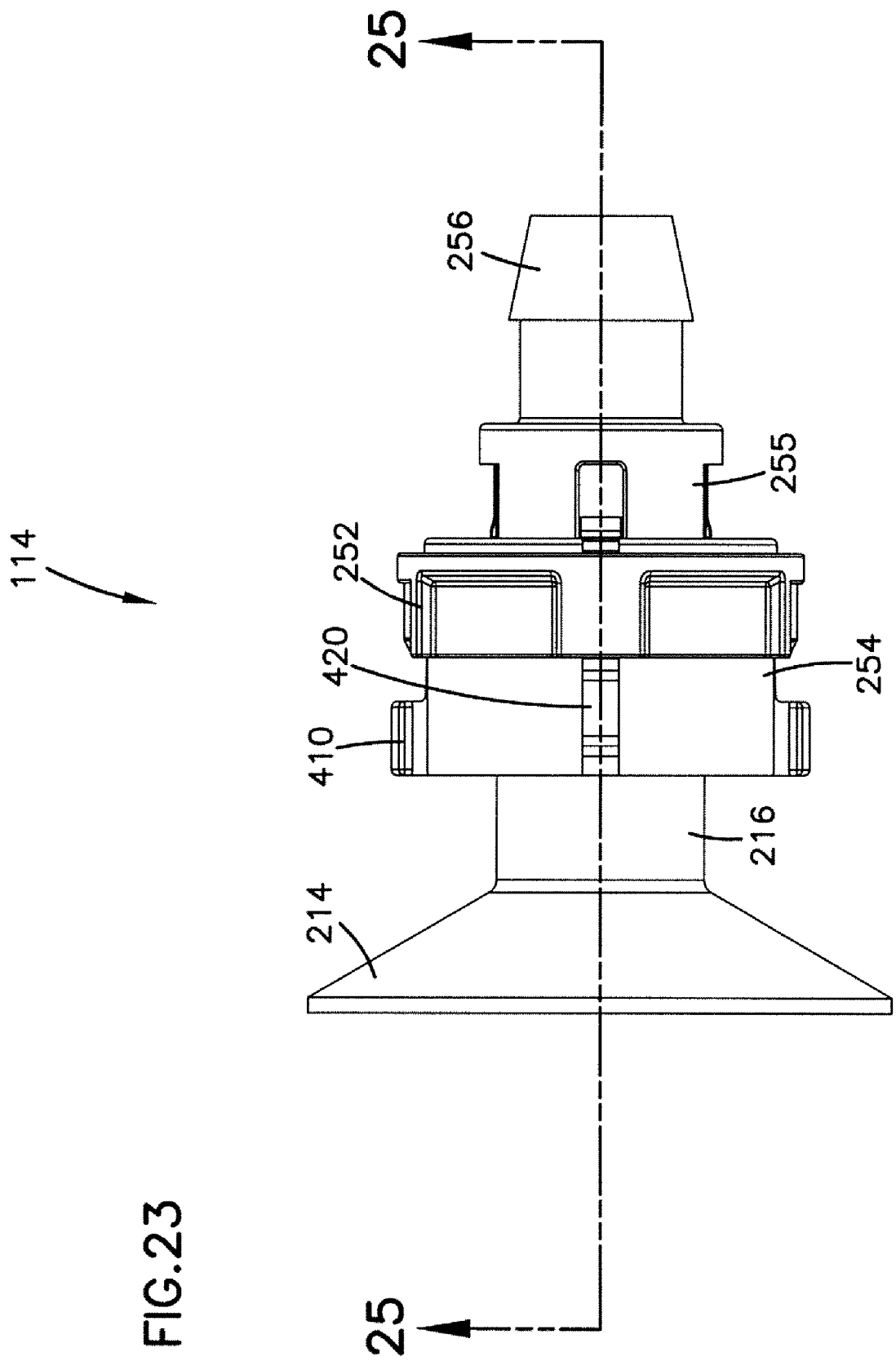
FIG. 23 shows a side view of the aseptic coupling device of FIG. 19.
Figure 24:
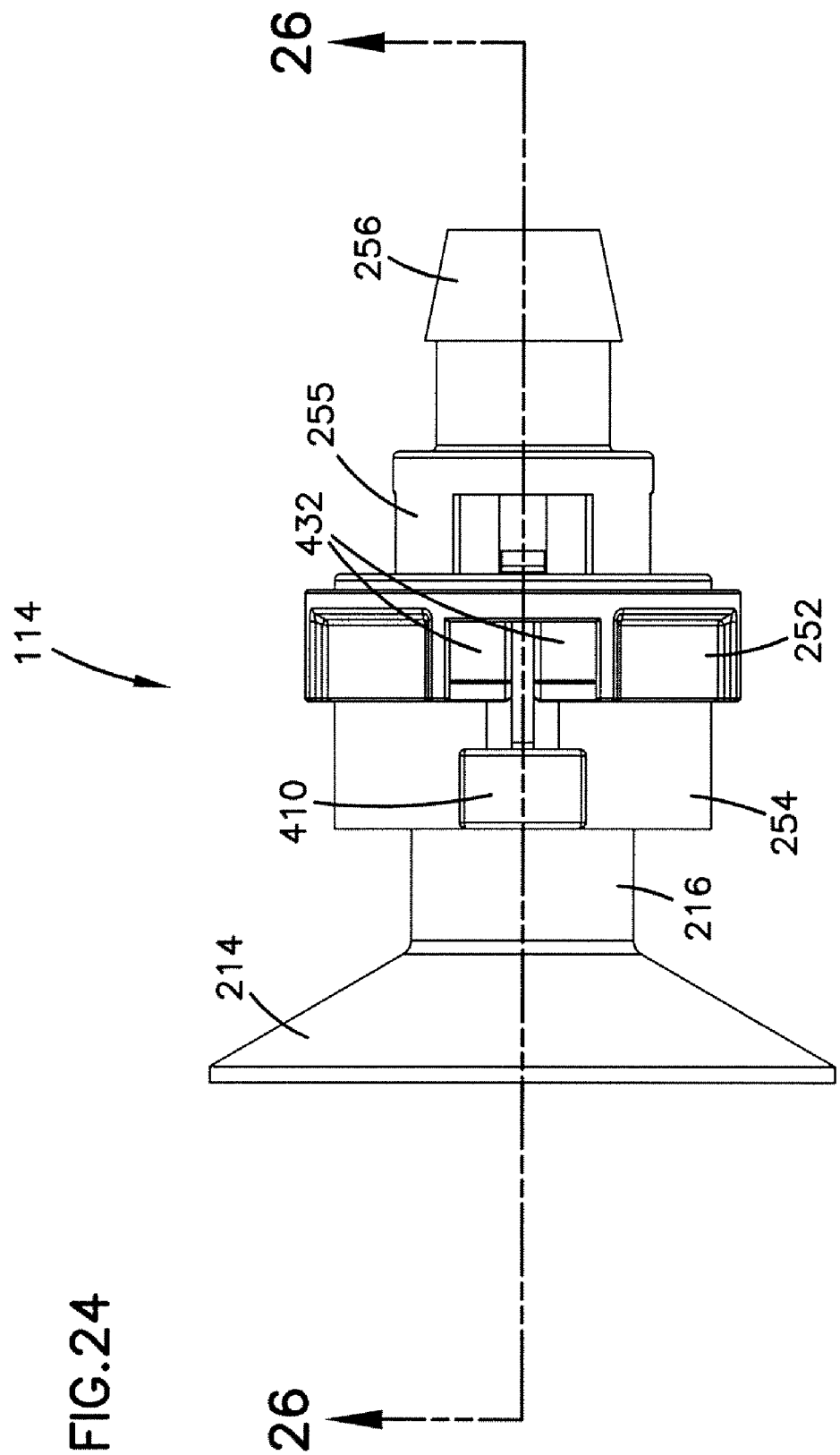
FIG. 24 shows another side view of the aseptic coupling device of FIG. 23.
Figure 25:
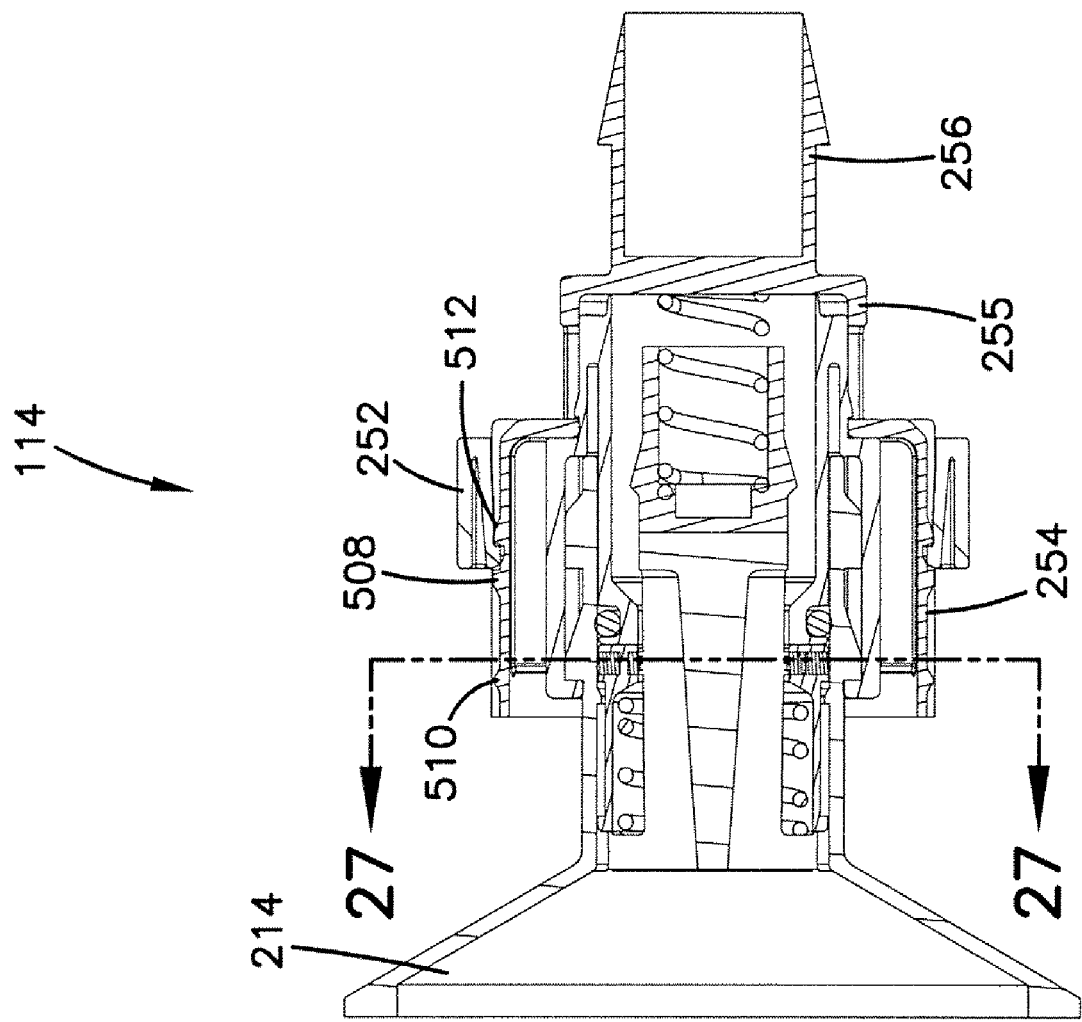
FIG. 25 shows a cross-sectional view of the aseptic coupling device of FIG. 23 along line 25-25.
Figure 26:
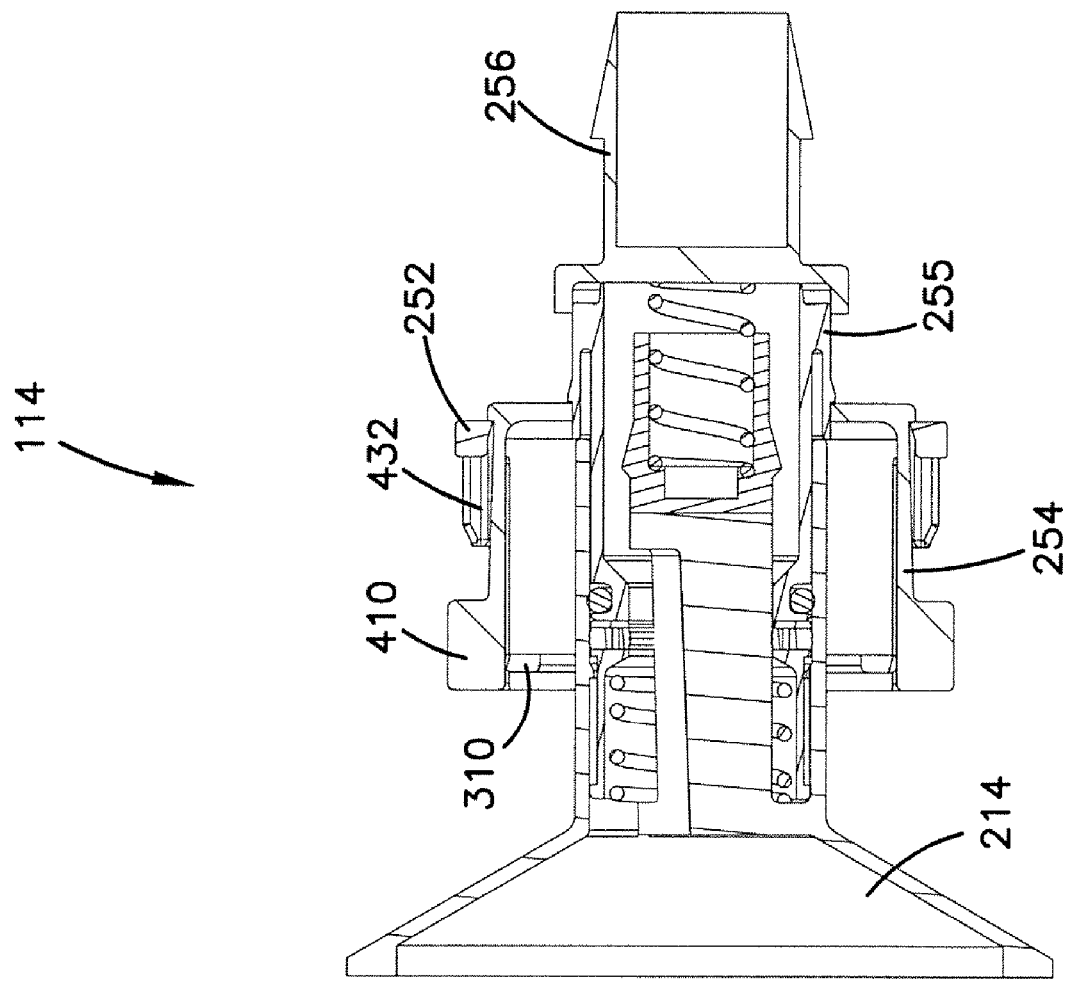
FIG. 26 shows a cross-sectional view of the aseptic coupling device of FIG. 24 along line 26-26.

As shown in FIG. 18, as first portion 210 moves relative to second portion 250 from the shipped state to the flow state, a front surface 502 of member 248 forces valve member 262 against spring 264 in an axial direction towards barb portion 256 of second portion 250 so that valve member 262 is unseated from seat portion 266. Likewise, a surface 506 of valve member 240 is forced by a surface 504 of main body 255 against spring 246 in an opposite axial direction towards front portion 212 of first portion 210. Seal portion 260 seals against interior surface 244 of main body 216 of first portion 210. In the flow state, fluid communication is created between flow paths 222, 258 of first and second portions 210, 250 so that a flow path A extends through aseptic coupling device 114 to allow fluid to flow therethrough.

As aseptic coupling device 114 is moved from the shipped state to the flow state, the sterility of fluid pathways 222, 258 through aseptic coupling device 114 is maintained.

Referring now to FIGS. 19-29, aseptic coupling device 114 can be moved from the flow state to a disconnected state to stop the flow of liquid through aseptic coupling device 114 and to disconnect first portion 210 from second portion 250. To in initiate this transition, collar portion 252 is slid or retracted axially from a locked position, shown in FIG. 18. Collar portion 252 moves along a groove 420 formed in front portion 254 toward barb portion 256 to an unlocked position, shown in FIG. 25.

A tab 508 of collar portion 252 engages a bead 510 formed in front portion 254 to define the locked position. As collar portion 252 is moved axially, tab 508 rides over bead 510 formed on front portion 254 and engages another bead 512 on front portion 254 to define the unlocked position.

Figure 27:
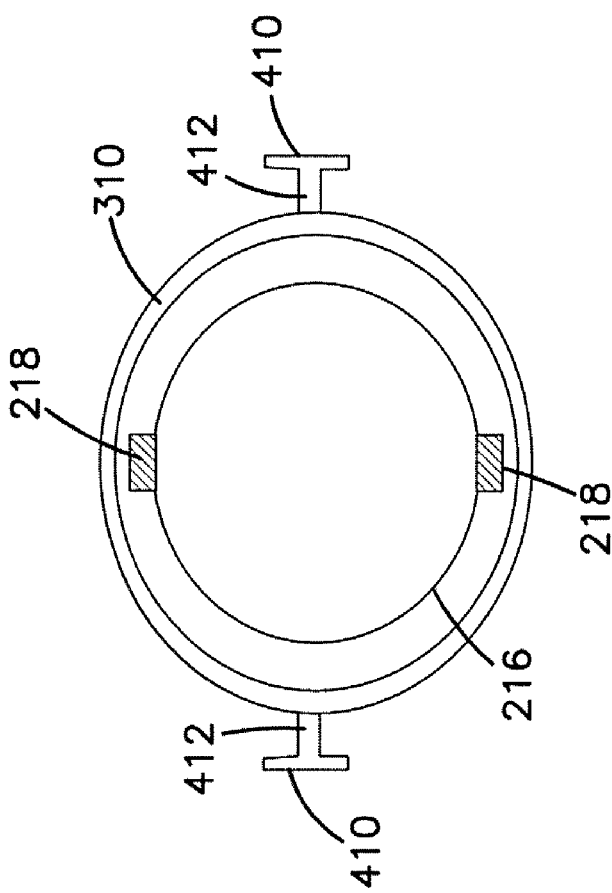
FIG. 27 shows a cross-sectional view of a portion of the aseptic coupling device of FIG. 25 along line 27-27.
Figure 28:
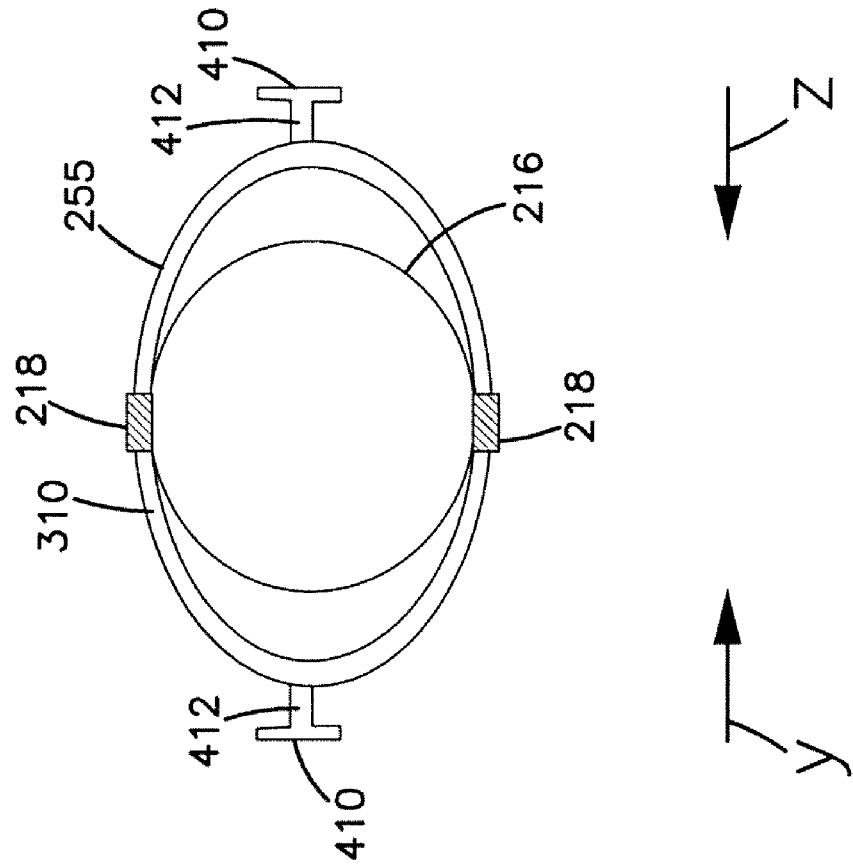
FIG. 28 shows another cross-sectional view of the portion of the aseptic coupling device of FIG. 27 with buttons of the aseptic coupling device in a depressed state.
Figure 29:
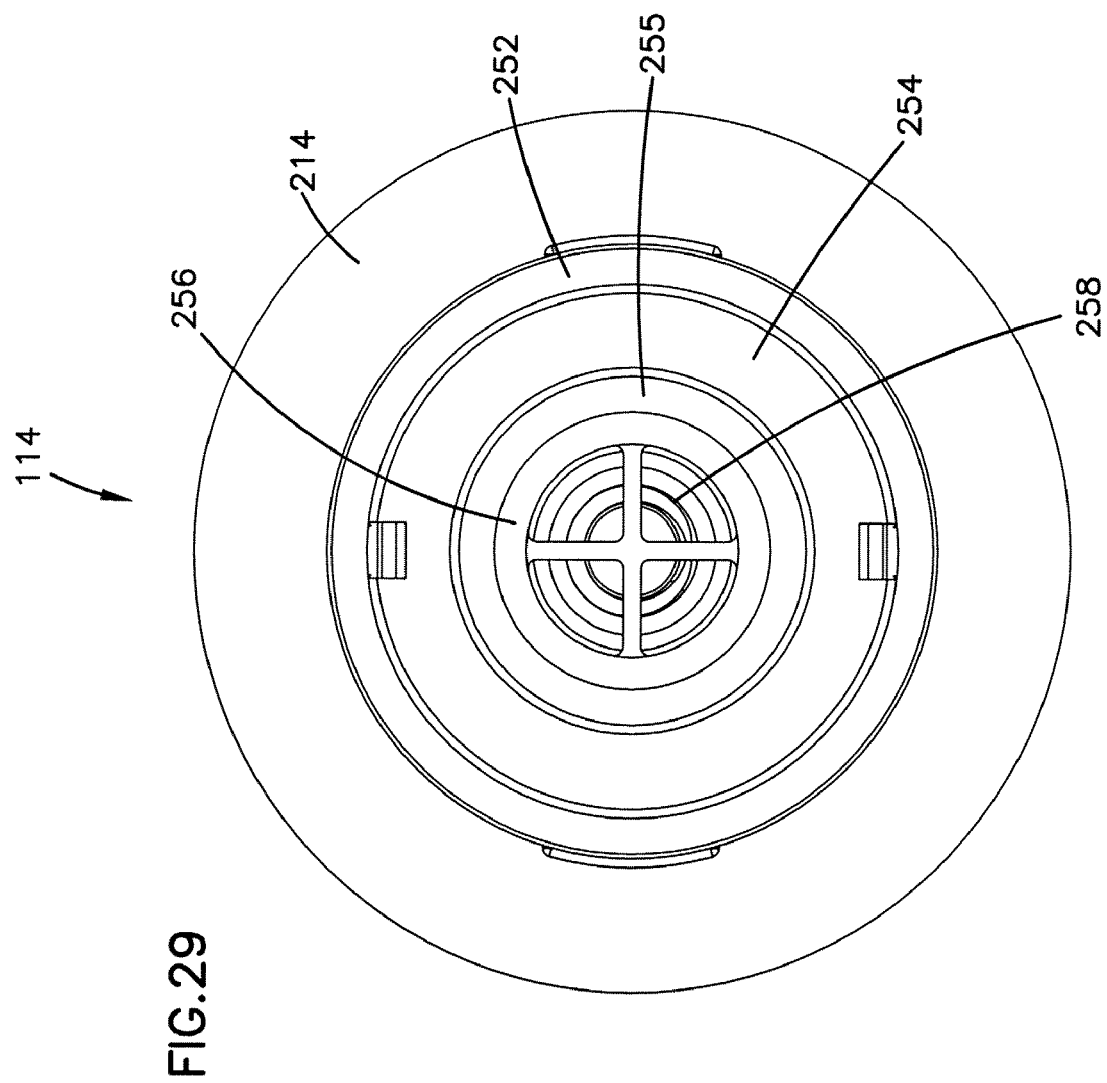
FIG. 29 shows an end view of the aseptic coupling device of FIG. 19.

As collar portion 252 moves axially from the locked to the unlocked position, seat portions 432 of collar portion 252 are moved from under buttons 410 formed on opposing sides of front portion 254. Buttons 410 include portions 412 (see FIGS. 21 and 22) that extend through a groove 434 formed between seat portions 432. When collar portion 252 is slid axially to a retracted position, as shown in FIGS. 19-26, seat portions 432 clear buttons 410. Buttons 410 can then be depressed radially so that portions 412 contact and deform lip 310 of main body 255. As shown in FIG. 27, lip 310 of main body 255 is generally formed in an oval shape. As portions 412 deform lip 310 by depressing buttons 410 in opposite directions Y and Z, lip 310 is moved into a more circular shape that increases the diameter of lip 310 adjacent to barbs 218. When buttons 410 are fully pressed as shown in FIG. 28, lip 310 clears ends 224 of buttons 218 to allow first portion 210 to slide axially out of second portion 250. As first portion 210 slides out of second portion 250, deformed lip 310 clears buttons 218 and 220 until first portion 210 reaches a disconnected state, as shown in FIG. 4.

As first portion 210 is slid axially out of second portion 250 into the disconnected state, valve member 262 is moved by spring 264 back to the position shown in FIG. 4. In this manner, fluid pathway 258 is closed, thereby stopping the flow of fluid through second portion 250 of aseptic coupling device 114 in the disconnected state.

In example embodiments, aseptic coupling device 124 is a typical aseptic coupling device that does not necessarily include valve member 240 or second portion 250. In alternative embodiments, aseptic coupling device 124 can be similar in construction to aseptic coupling device 114.

In one example method of use, aseptic coupling device 114 is connected to aseptic coupling device 124. Next, aseptic coupling device 114 is moved from the shipped state to the flow state to allow fluid flow therethrough. Subsequently aseptic coupling device 114 is moved to the disconnected state to stop the flow of fluid therethrough.

In example embodiments, the aseptic coupling devices are made of a polymeric material. For example, in one embodiment, the aseptic coupling devices are made of polycarbonate and the seals used therein are made of a silicone rubber. Other materials can be used.

The various embodiments described above are provided by way of illustration only and should not be construed to limiting. Those skilled in the art will readily recognize various modifications and changes that may be made to the embodiments described above without departing from the true spirit and scope of the disclosure or the following claims.

What is claimed is:

1. An aseptic coupling device, comprising:
   a front portion defining a front surface configured to create a sterile connection with a mating aseptic coupling device, the front portion including a front valve member defining open and closed positions;
   a rear portion including a rear valve member defining open and closed positions;
   a button member that, when actuated, allows movement of the rear portion relative to the front portion;
   a collar member positioned relative to the button member to restrict movement of the button member when the collar member is in a locked position, and to allow movement of the button member when the collar member is in an unlocked position;
   wherein the front portion is coupled to the rear portion in a first position such that the front valve member and the rear valve member do not allow fluid flow through the front portion and the rear portion;
   wherein the front portion is axially movable relative to the rear portion to a second position to allow fluid flow through the front portion and the rear portion; and
   wherein, when the collar member is moved to the unlocked position and the button member is actuated, the rear portion is movable axially relative to the front portion such that the front portion is disconnected from the rear portion, and the rear valve member does not allow fluid flow through the rear portion.

2. The device of claim 1, wherein the front portion includes an apparatus configured to be connected to a second aseptic coupling device to form the sterile connection.

3. The device of claim 1, wherein the collar member defines a seat portion such that, when the collar member is in the locked position, the seat portion is positioned relative to the button member to restrict movement of the button member, and wherein, when the collar member is moved axially into the unlocked position, the seat portion is moved relative to the button member to allow movement of the button member.

4. The device of claim 3, wherein the button member is configured to move transversely relative to axial movement of the collar member.

5. The device of claim 4, wherein the seat portion of the collar member is positioned to limit transverse movement of the button member when the collar member is in the locked position.

6. The device of claim 1, wherein the rear portion is configured to be moved multiple times relative to the front portion between the first and second positions.

7. The device of claim 1, further comprising a membrane coupled to the front surface of the front portion, wherein the membrane is configured to roll out of the aseptic coupling device along with a corresponding membrane on the mating aseptic coupling device to form the sterile connection.

8. An aseptic coupling device, comprising:
   a front portion defining a front surface configured to create an aseptic connection with a mating aseptic coupling device so that a sterile fluid pathway is formed between the aseptic coupling device and the mating aseptic coupling device;
   a front valve member positioned in the front portion to define open and closed positions;
   a rear portion;
   a rear valve member positioned in the rear portion to define open and closed positions;

a button member that, when actuated, allows movement of the rear portion relative to the front portion;

wherein, with the front portion coupled to the rear portion, the front valve member and the rear valve member are axially moveable to allow fluid flow through the front portion and the rear portion; and wherein, when the button member is actuated, the rear portion is movable axially relative to the front portion such that the front portion is disconnected from the rear portion, and the rear valve member does not allow fluid flow through the rear portion.

9. The device of claim 8, further comprising a membrane coupled to the front surface of the front portion, wherein the membrane is configured to roll out of the aseptic coupling device along with a corresponding membrane on the mating aseptic coupling device to form the aseptic connection.

10. The device of claim 8, wherein, when the front portion is disconnected from the rear portion, the front valve member does not allow fluid flow through the front portion.

11. The device of claim 8, further comprising a collar member positioned relative to the button member to restrict movement of the button member when the collar member is in a locked position, and to allow movement of the button member when the collar member is in an unlocked position.

\* \* \* \* \*